(12) United States Patent
Berg et al.

(10) Patent No.: US 11,280,742 B2
(45) Date of Patent: Mar. 22, 2022

(54) ANALYTE MEASURING SYSTEM AND METHOD

(71) Applicant: Roche Diabetes Care, Inc., Indianapolis, IN (US)

(72) Inventors: Max Berg, Mannheim (DE); Fredrik Hailer, Mannheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 0 days.

(21) Appl. No.: 16/759,505

(22) PCT Filed: Oct. 25, 2018

(86) PCT No.: PCT/EP2018/079267
§ 371 (c)(1),
(2) Date: Apr. 27, 2020

(87) PCT Pub. No.: WO2019/081632
PCT Pub. Date: May 2, 2019

(65) Prior Publication Data
US 2020/0309710 A1 Oct. 1, 2020

(30) Foreign Application Priority Data
Oct. 26, 2017 (EP) .................................... 17198674

(51) Int. Cl.
*G01N 21/84* (2006.01)
*G01N 21/31* (2006.01)
(Continued)

(52) U.S. Cl.
CPC ....... *G01N 21/8483* (2013.01); *G01N 21/314* (2013.01); *G01N 33/4875* (2013.01);
(Continued)

(58) Field of Classification Search
CPC .............. G01N 21/8483; G01N 21/78; G01N 33/48764; G01N 35/00009;
(Continued)

(56) References Cited

U.S. PATENT DOCUMENTS

2006/0173380 A1* 8/2006 Hoenes ............ G01N 35/00009
600/583
2007/0020143 A1 1/2007 Seidenstricker et al.
(Continued)

FOREIGN PATENT DOCUMENTS

CA         2567675 C  *  9/2010  ....... G01N 35/00009
WO    WO-2014122324 A1 *  8/2014  ....... A61B 5/150358

*Primary Examiner* — Michael P Stafira
(74) *Attorney, Agent, or Firm* — Woodard, Emhardt, Henry, Reeves & Wagner, LLP

(57) ABSTRACT

The invention concerns an analyte measuring system comprising a test tape (22) having a plurality of functional elements (20) including a test field (46), a further comprising a meter (12) having a tape drive (24) operable to advance the test tape (22), a light source (30) adapted to illuminate at least one measuring spot at a measuring position, and a measuring engine (32) to receive optical signals from the at least one measuring spot for detection of the analyte in the body fluid. For tape positioning, it is proposed that the measuring engine (32) comprises a signal processor (34) operable to determine if a test field (46) is in the measuring position, said determination comprising an identification of a pre-determined distance between at least two functional elements (20) in the optical signals obtained while advancing the test tape (22).

22 Claims, 3 Drawing Sheets

(51) Int. Cl.
*G01N 33/487* (2006.01)
*G01N 33/49* (2006.01)

(52) U.S. Cl.
CPC ..... *G01N 33/49* (2013.01); *G01N 2021/3181* (2013.01); *G01N 2201/062* (2013.01)

(58) Field of Classification Search
CPC ......... G01N 2035/00019; G01N 33/66; G01N 15/1404; G01N 15/1468; G01N 15/147; G01N 2015/0065; G01N 2015/1452; G01N 33/5091; G01N 33/5094; G01N 33/49; G01N 33/525; G01N 15/06; G01N 15/1434; G01N 15/1463; G01N 15/1475; G01N 1/30; G01N 2015/1037; G01N 2015/1411; G01N 2015/1413; G01N 2015/1486; G01N 2021/058; G01N 21/53; G01N 2201/12; G01N 33/4915; G01N 33/80; G01N 2021/7786; G01N 21/55; G01N 21/6428; G01N 2201/0221; G01N 2001/028; G01N 2021/7769; G01N 21/17; G01N 21/75; G01N 27/3272; G01N 27/3274; G01N 33/48; G01N 2021/8488; G01N 2021/8557; G01N 21/274; G01N 33/52; G01N 2035/00108; G01N 21/4738; G01N 21/77; G01N 33/4875; G01N 33/48757; G01N 33/521; G01N 33/526; G01N 33/558; G01N 35/00663; G01N 2021/6439; G01N 2021/7759; G01N 2035/00168; G01N 2035/00673; G01N 2035/00752; G01N 2201/0612; G01N 2201/0621; G01N 2201/0697; G01N 2333/904; G01N 2333/90616; G01N 27/12; G01N 33/48778; G01N 33/492; G01N 35/00029; G01N 2021/3155; G01N 2021/3181; G01N 2021/478; G01N 2021/8494; G01N 2021/8654; G01N 2035/00148; G01N 2035/0851; G01N 2035/0491; G01N 21/253; G01N 21/314; G01N 21/3151; G01N 2201/062; G01N 2201/0696; G01N 2333/70596; G01N 2800/044; G01N 33/487; G01N 33/50; G01N 33/54346; G01N 33/574; G01N 33/92; G01N 35/02; G01N 35/00; G01N 2021/6436; G01N 21/86; G01N 33/53; G01N 2201/13; G01N 27/3273; G01N 21/25; G01N 33/48785; G01N 33/538; G01N 33/54386; G01N 2021/315; G01N 2201/06193; G01N 35/00732; G01N 21/31; G01N 2021/7766; G01N 2021/7796; G01N 27/72; G01N 33/552; G01N 33/68; G01N 2400/00; G01N 33/48707; G01N 33/54366; G01N 2035/00039; G01N 21/00; G01N 21/7703; G01N 21/85; G01N 21/898; G01N 33/48792; G01N 33/5302; G01N 33/946; G01N 33/948; G01N 35/04; G01N 2333/02; G01N 33/48771; G01N 33/54306; G01N 33/5438; G01N 33/689; G01N 33/94; G01N 35/1016; G01N 2035/00089; G01N 21/27; G01N 21/84; G01N 23/00; G01N 2333/185; G01N 2458/40; G01N 27/44704; G01N 27/44782; G01N 27/44791; G01N 30/02; G01N 30/30; G01N 30/90; G01N 31/22; G01N 33/533; G01N 33/543; G01N 33/582; G01N 33/587; G01N 33/721; G01N 33/723; G01N 2015/0693; G01N 2015/1006; G01N 2015/1497; G01N 2021/0325; G01N 2021/1765; G01N 2021/6484; G01N 2021/772; G01N 2021/7773; G01N 2035/00564; G01N 2035/0436; G01N 21/03; G01N 21/0303; G01N 21/251; G01N 21/474; G01N 21/64; G01N 21/6486; G01N 21/80; G01N 2201/08; G01N 2201/125; G01N 2201/129; G01N 2223/076; G01N 2223/303; G01N 2223/507; G01N 23/223; G01N 2333/11; G01N 2333/16; G01N 2333/20; G01N 2333/4737; G01N 2469/20; G01N 27/02; G01N 27/22; G01N 27/30; G01N 27/327; G01N 27/3271; G01N 27/3276; G01N 27/33; G01N 27/3335; G01N 27/414; G01N 2800/26; G01N 2800/50; G01N 31/223; G01N 31/224; G01N 33/00; G01N 33/0009; G01N 33/483; G01N 33/491; G01N 33/54373; G01N 33/54393; G01N 33/554; G01N 33/559; G01N 33/564; G01N 33/56988; G01N 33/571; G01N 33/5764; G01N 33/583; G01N 33/6854; G01N 33/6893; G01N 35/0099; G01N 35/10; G01N 35/1004; G01N 35/1067

See application file for complete search history.

(56) References Cited

U.S. PATENT DOCUMENTS

| | | | |
|---|---|---|---|
| 2007/0171398 A1* | 7/2007 | Petrich | G01N 35/00009 356/39 |
| 2007/0217950 A1* | 9/2007 | Kramer | G01N 35/00009 422/66 |
| 2008/0049227 A1* | 2/2008 | Sacherer | G01N 21/8483 356/445 |
| 2009/0212109 A1* | 8/2009 | Harttig | G06K 19/06046 235/454 |
| 2011/0108190 A1* | 5/2011 | Dagenbach | B32B 38/1858 156/238 |
| 2011/0243810 A1* | 10/2011 | Schosnig | G01N 35/00009 422/400 |
| 2011/0263957 A1* | 10/2011 | Thoes | G01N 33/48764 600/365 |
| 2011/0273715 A1* | 11/2011 | Seelig | G01N 33/48764 356/445 |
| 2012/0006105 A1* | 1/2012 | Zimmer | G01N 35/00009 73/61.59 |
| 2012/0010489 A1* | 1/2012 | Miltner | A61B 5/1455 600/365 |
| 2012/0043376 A1* | 2/2012 | Petrich | G06K 19/06046 235/375 |
| 2012/0045842 A1* | 2/2012 | Petrich | G01N 33/48764 436/95 |
| 2012/0055606 A1* | 3/2012 | Schwoebel | B05C 11/00 156/60 |
| 2012/0241335 A1* | 9/2012 | Horn | G01N 33/48757 206/216 |
| 2017/0205343 A9 | 7/2017 | Kramer et al. | |

* cited by examiner

ANALYTE MEASURING SYSTEM AND METHOD

FIELD OF THE INVENTION

The invention concerns an analyte measuring system comprising a test tape having a plurality of functional elements arranged thereon, the functional elements comprising at least a test field onto which a body fluid can be applied by a user, and further comprising a meter, preferably a handheld meter, the meter comprising a tape drive operable to advance the test tape, such that the functional elements can be successively positioned in a measuring position, the meter further comprising a light source adapted to illuminate at least one measuring spot at the measuring position, and a measuring engine configured to receive optical signals from the at least one measuring spot for detection of the analyte in the body fluid. The invention is further directed to an analyte measuring method for use in such a system.

In the field of blood glucose testing, it is known to use disposable test elements in a handheld glucose meter for measurements on the spot. The user provides a fresh blood sample by pricking a finger and transferring a drop of blood onto the test element. Specifically, a plurality of test elements can be provided for successive use on a test tape, which is loadable into the meter in the form of a replaceable tape cassette. Thus, the user has no need to take care of the disposal of each single test element.

In current systems on the market, namely the Roche product Accu-Chek Mobile®, a separate position detector in addition to the analyte detector is used to determine and control positioning of functional elements on the tape, such as the test and calibration fields. The position detector is provided in a defined distance to the analyte detector. Thus, a corresponding fixed distance of position marks on the tape must be maintained. Further, the additional components of the position detector are a potential source of defects, are costly and need additional construction space.

EP 1 785 730 A1 describes a fine positioning of the wetting area of a test field at the measuring site by means of a photometric positioning device. This document further mentions that, in principle, the sensor of the positioning device could also be used to detect the target signal in addition to the wetting. However, in order to meet the various requirements, it would be expedient to use a separate detector for this purpose.

On this basis an object of the invention is to further improve the known analyte test systems and methods to achieve improved design flexibility and simplification while guaranteeing a robust and exact tape positioning.

The combination of features stated in the independent claims is proposed to achieve this object. Advantageous embodiments and further developments of the invention are derived from the dependent claims.

BRIEF SUMMARY OF THE INVENTION

The present invention is based on the idea that precise tape positioning can be achieved by using the analyte detection optics also for controlling tape advancement, wherein a pre-determined distance between two functional elements on the tape is detected in the recorded signals. Consequently, it is proposed according to the invention that the measuring engine comprises a signal processor operable to determine if a test field is in the measuring position, said determination comprising an identification of a pre-determined distance between at least two functional elements in the optical signals obtained while advancing the test tape. In this way, a separate positioning device is obsolete. The signal processor can be programmed to account for various tape designs, thus maintaining compatibility with current products and allowing positioning even without positioning marks. In fact, in a very minimalist design, only the distance between consecutive analyte test fields may be used for determining the measuring position.

Preferably, the light source is configured to illuminate at least two essentially non-overlapping measuring spots which are arranged one after another in the direction of tape transport. This allows for a check of the correct transport direction and/or for a more robust discrimination of interfering influences, including e.g. ageing.

For additional measuring advantages, it is further expedient that all of the measuring spots are arranged on one functional element when said functional element is provided in the measuring position.

According to a preferred implementation of a multiple pointed light source, one or more LEDs are used to illuminate a distinct measuring spot in each case.

In this context, it is further advantageous if at least two LEDs are provided which emit at different wavelengths, preferably one wavelength in the visible region (400-750 nm) and one wavelength in the infrared region (more than 750 nm). In this way, it is also possible to make further plausibility checks in regard of expected signal intensities.

In order to avoid a sluggish behavior and to enable fast-acting control of tape advancement, it is advantageous when the measuring engine has a sampling frequency in the range of milliseconds, i.e. 1 to 100 milliseconds, and preferably about 10 milliseconds, to record the optical signals.

For a detection of the transition from an unstructured tape section to a test element and vice versa, it is purposive if the signal processor is operable to evaluate differences between the optical signals obtained from each of at least two measuring spots.

As a still further advantageous measure, the signal processor should be operable to evaluate one or more derivatives of said differences between the optical signals.

According to a preferred implementation, the signal processor is operable to derive a distance between at least two functional elements from a speed of the tape transport and a time period between consecutive edges of signal peaks in the optical signals.

Furthermore, and in particular for the purpose stated above, the signal processor may comprise a comparator to compare a distance between two functional elements, said distance being derived from the optical signals, to a pre-determined distance between two functional elements, wherein, if appropriate, a tolerance is taken into account.

A still further improvement provides for the signal processor to be adapted to stop the tape drive when having determined that a test field is in the measuring position.

For a plausibility check of the tape positioning, the signal processor may be operable to determine a difference in signal level or in height of the optical signals received from two measuring spots which are illuminated at different wavelengths.

For further purposes like calibration of the measuring engine, it is advantageous if the functional elements comprise reflective fields, each of which is arranged between successive test fields, and if the test tape is positioned in a standby state when a reflective field is in the measuring position.

In a preferred embodiment, the body fluid is blood; the analyte preferably is blood glucose.

Another aspect of the invention concerns an analyte measuring method comprising the steps of providing a test tape having a plurality of functional elements arranged thereon, the functional elements comprising at least a test field onto which a body fluid can be applied by a user;

advancing the test tape in a meter, preferably a handheld meter, such that the functional elements are successively transported to a measuring position; illuminating at least one measuring spot on a functional element at the measuring position;

receiving optical signals from the at least one measuring spot for detection of the analyte in the body fluid;

determining, from the optical signals obtained while advancing the test tape, if a test field is in the measuring position, wherein said determination step comprises identifying a pre-determined distance between at least two functional elements on the basis of the optical signals.

In this way, the same positive effects and benefits can be achieved as described herein above in connection with the features of the system, any of which features may be combined, in an analogous way, with the method according to the invention.

BRIEF DESCRIPTION OF THE SEVERAL VIEWS OF THE DRAWINGS

In the following, the invention is further elucidated on the basis of an embodiment example shown schematically in the drawings, where.

DETAILED DESCRIPTION OF THE INVENTION

Figure 1:
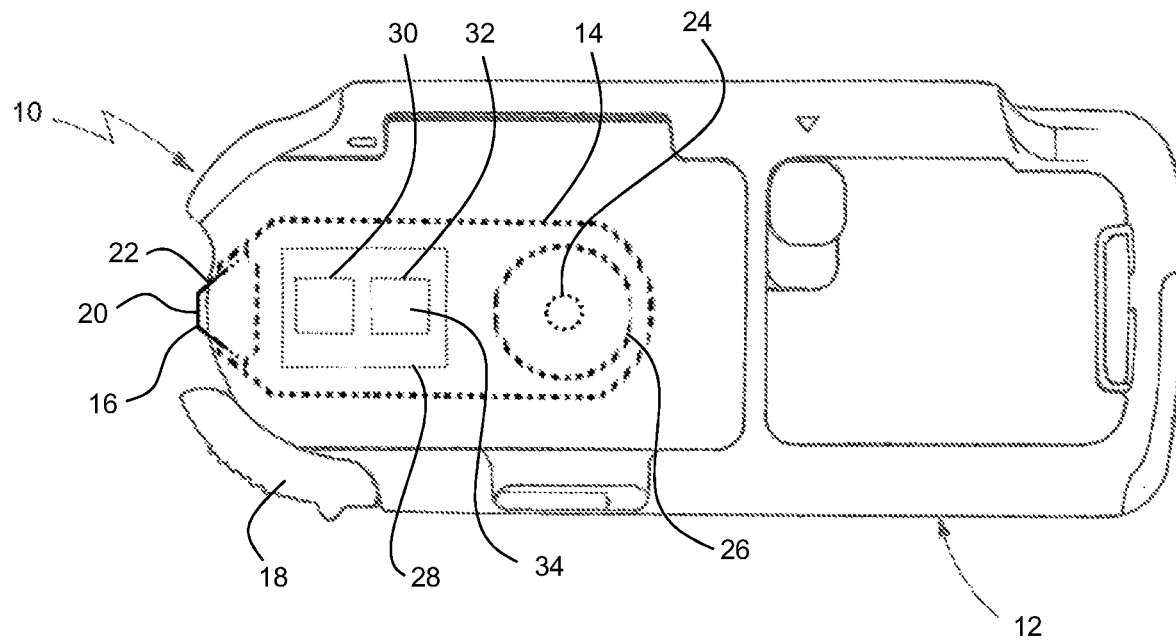
FIG. 1 is a bottom view of a handheld blood glucose meter including a test tape cassette.

In the drawings, an exemplary embodiment of a medical analyte measuring system for testing an analyte in a body fluid, specifically glucose in a blood sample is shown.

As depicted in FIG. 1, the system 10 at least comprises a portable blood glucose meter 12 adapted to receive a disposable test tape cassette 14 which can be inserted into a compartment of the meter 12. A deflection tip 16 of the inserted tape cassette 14 is accessible to the user upon opening a tip cover 18. The tape cassette 14 serves as a test magazine, as a plurality of functional elements 20 is provided on a spoolable test tape 22 for successive use on the deflection tip 16. For this purpose, the meter 12 comprises a rotatable drive pinion 24 which engages a take-up reel 26 of the tape cassette 14.

The handheld meter 12 is further provided with a photometric measuring unit 28 comprising a light source 30 and a measuring engine 32 for determining the concentration of the analyte (glucose) from detected optical signals. The test result can be displayed to the user on a display which is arranged on the top side of the meter 12 (not shown).

The measuring engine 32 includes a photodetector and signal processor 34 (electronic micro-processor) which is operable to determine if a functional element 20 is in the measuring position on the deflection tip 16, as further explained below. In this position, the user can apply a sample of body fluid, i.e. a drop of blood, onto the upper side of a functional element 20 which is formed as a chemistry test field and is responsive to the analyte by a color change. The optical signals are taken from the rear side of the transparent test tape 22 through a measuring window of the tip 16.

Figure 2:
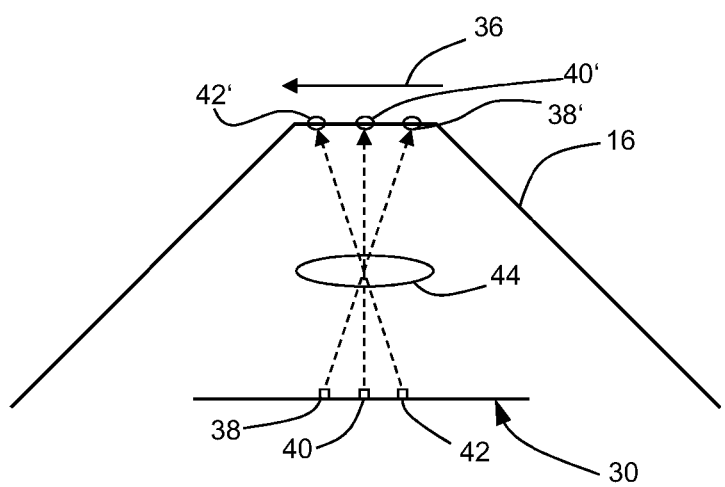
FIG. 2 is a schematic view of a light source of the meter for providing three measuring spots on the test tape.

FIG. 2 schematically illustrates the spatial configuration of the light source 30 with respect to the deflection tip 16 and the test tape 22 guided thereon in direction of arrow 36 during tape transport.

The light source 30 comprises three light-emitting diodes (LEDs) 38, 40, 42 that are arranged in a row in the direction of tape transport and are imaged consecutively as corresponding light or measuring spots 38',40',42' by a collecting lens 44. The measuring spots 38',40',42' are distinct, i.e. spaced apart from each other, but within the dimensions of a test element 20 used for analyte detection when positioned on the tip 16.

In order to allow an assignment of the respective optical signals using only one sensor, the LEDs 38, 40, 42 can be actuated separately from one another. Then, the measuring engine should have a sampling frequency in the range of 1 to 100 milliseconds, e.g. 10 milliseconds, to provide a sufficient time resolution also for tape positioning. It is further expedient when the center LED 40 emits in the visible region (e.g. at 650 nm), whereas the outer LEDs 38, 42 emit in the infrared region (e.g. 875 nm). This allows to evaluate the level or signal height of the obtained optical signals for identifying a structure or wetting of different test elements 20.

Figure 3:
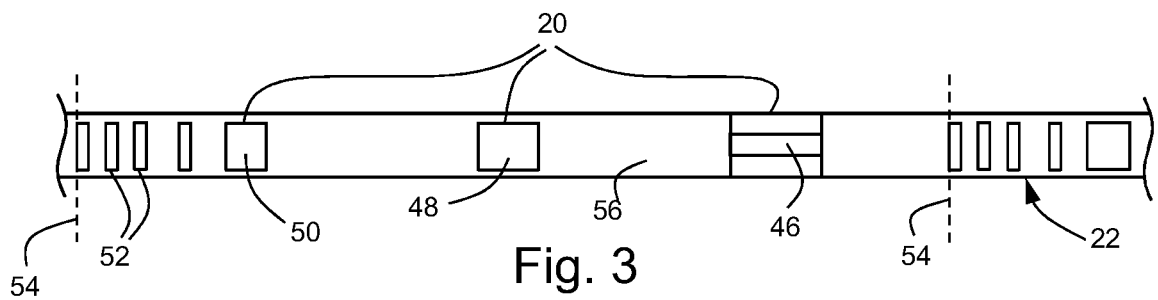
FIG. 3 shows a section of the test tape having various functional elements including a test field.

As shown in FIG. 3, the functional elements 20 comprise test pads or fields 46 that are located individually each on an assigned tape section. These test fields 46 are formed by a layered chemistry field which is bordered by hydrophobic edge strips. Each section of the test tape 22 is additionally provided with a reflective white field 48 and a stop mark 50 for the white field 48. A positioning code in the form of various position markers 52 is intended for compatibility with previous system designs, as disclosed in WO 2010/043655 A1. The functional elements 20 described above are repeated on each tape section 54 that is furnished with a test field 46 so that at a given length of the section for example 50 tests can be stored in a tape cassette 14. It should be noted that the functional elements 20 are separated at a distance from each other by tape segments 56 which have no specific structure.

Figure 4:
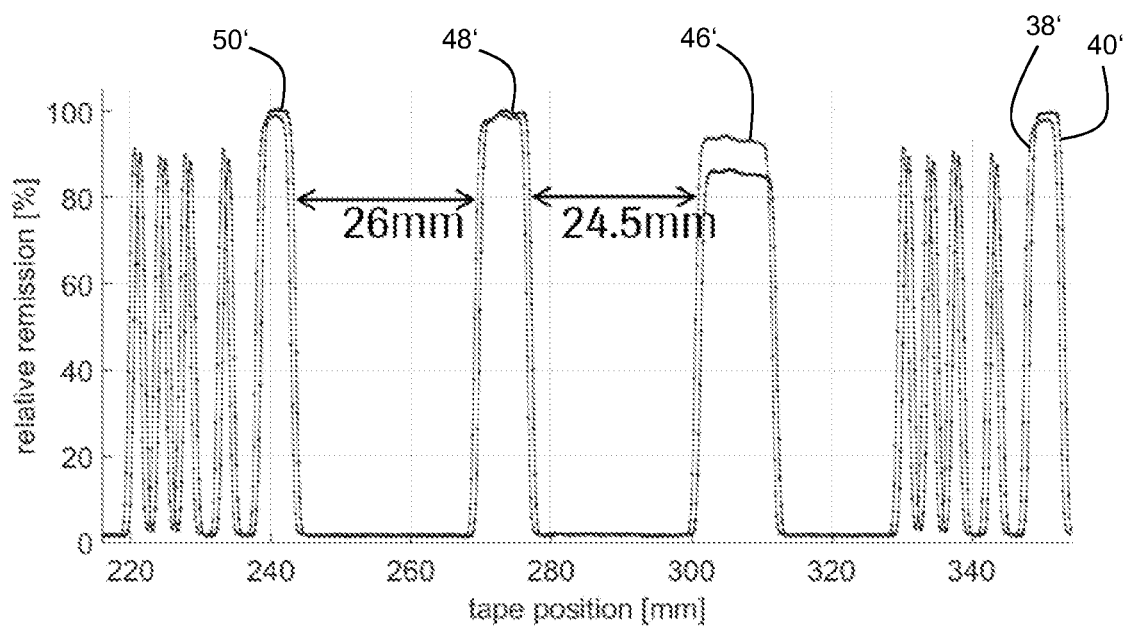
FIG. 4 is a diagram of optical signals obtained from two of the measuring spots while advancing the test tape.

FIG. 4 shows the reflection signals (normalized as relative remission) obtained from measuring spots 38' and 40' during movement of the tape part of FIG. 3 over the tip 16. The distance d between two measuring points on the abscissa is calculated from the revolution speed n of the drive pinion 24 and the actual diameter d of the tape wrap on the take-up spool 26, the latter being proportional to the number of already used test fields 46, while further accounting for the sampling rate t, according to d=n*nd/t.

Due to the spatial distance of measuring spots 38', 40', the recorded signal curves are correspondingly displaced in their x-coordinates. In the transparent sections of the test tape 22, the reflection is nearly zero, whereas the white field 48 reflects nearly all of the irradiated light in both of the visible and infrared region. Thus, the white field 48 can be used for calibration purposes. In contrast thereto, the chemistry of the test field 46 has a higher infrared reflectance as compared to the visible range (about 400 nm to 750 nm), which allows for a distinction or confirmation of proper tape positioning.

In the normal standby state, a white field 48 is positioned on the tip 16. In the active state, the next test field 46 on the tape is positioned in the measuring position on the tip 16 for sample application and analyte detection. The signal processor 34 is used for both positioning tasks, where predetermined distances to the preceding functional element 20 are determined in the optical signals. In the example shown in FIG. 3, the distance between the stop mark 50 and the white field 48 is 26 mm, and the distance between the white field 48 and the test field 46 is 24.5 mm. In FIG. 4, the signal peaks 46', 48', 50' can be assigned to the test field 46, white field 48 and stop mark 50. Thus, the respective distances are identifiable between the edges or slopes of consecutive peaks 46',48' and 48',50', as marked in FIG. 4.

In case that one of said distances including a given tolerance is observed, a digital comparator of the signal processor 34 decides that the standby or active position is reached, and consequently stops the rotation of the drive pinion 24.

Figure 5:
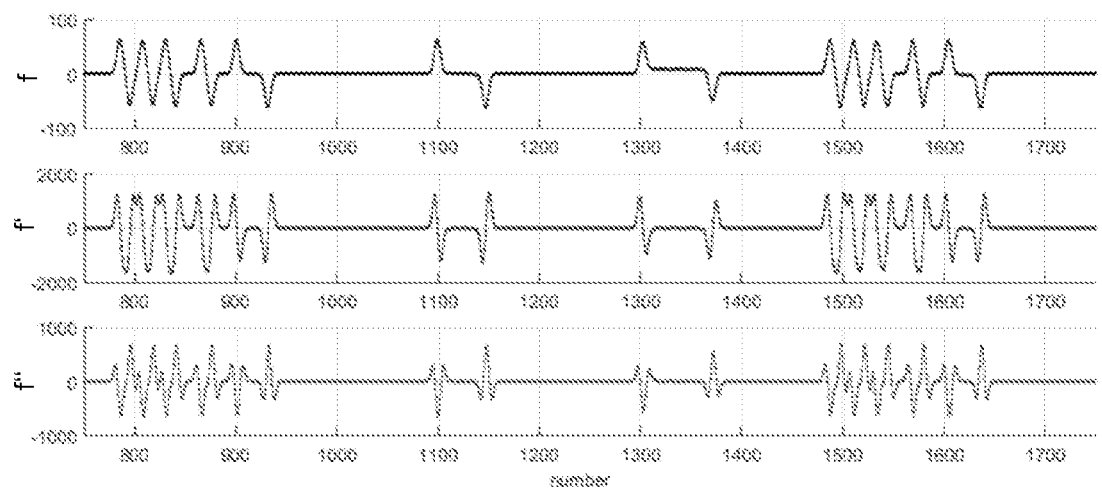
FIG. 5 is a diagram of the difference between the optical signals of FIG. 4 and first and second derivatives thereof.

As shown in FIG. 5, for a more robust detection of signal edges, the signal processor 34 is operable to evaluate the difference f of the signals in FIG. 4 and the first derivative f' and second derivative f" of said differences. The abscissae denote consecutive numbers of values according to the sampling rate.

Figure 6:
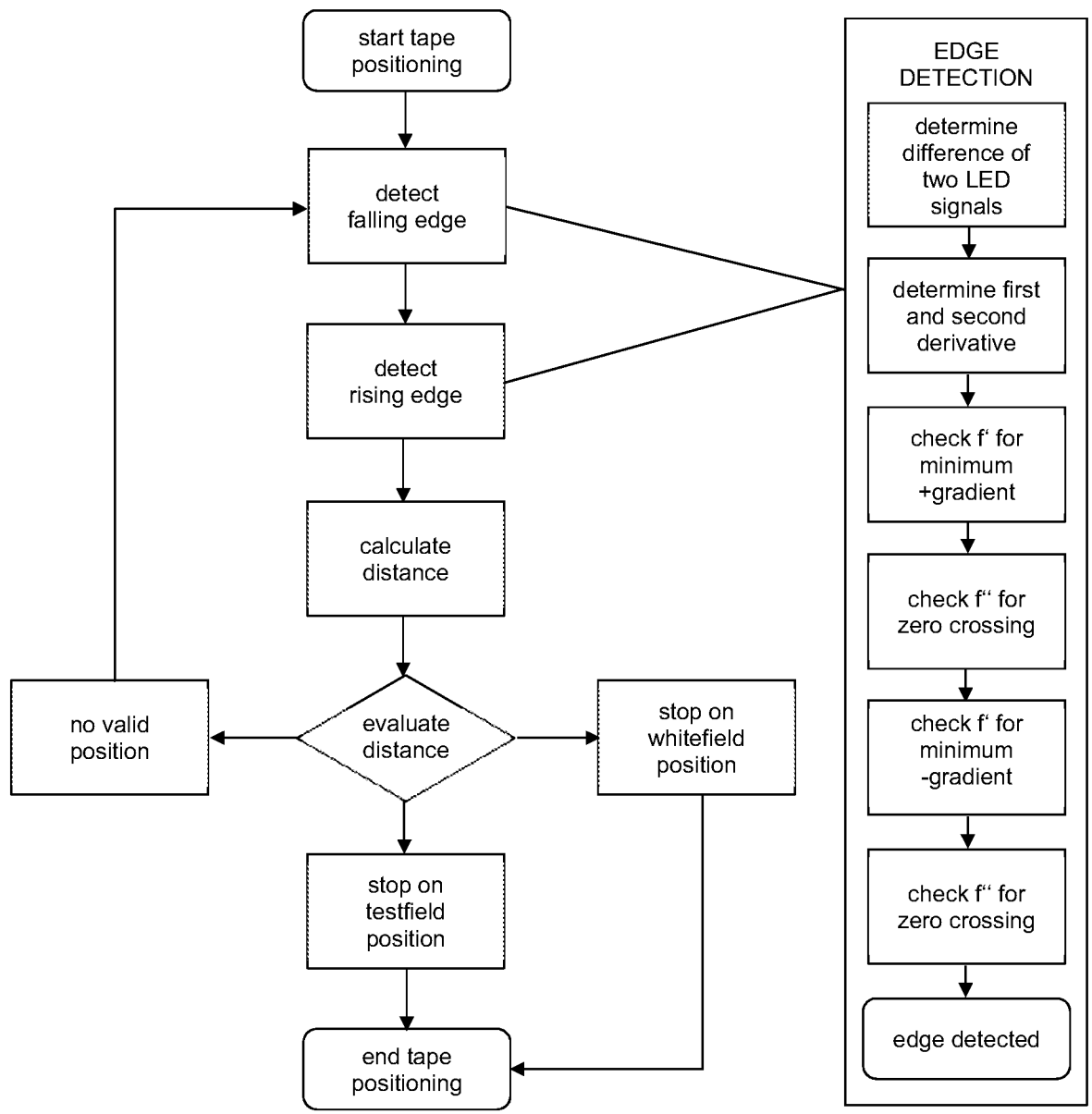
FIG. 6 is a flow-chart of the operation of a signal processor in the meter for determining if a functional field is in the measuring position.

FIG. 6 illustrates in a flow-chart a method for tape positioning using an edge detection in the optical signals. A falling edge occurs during tape movement from a functional element 20 to a transparent tape section 56 at the measuring position. For the detection of a falling edge, the signal processor 34 runs the routine EDGE DETECTION, as illustrated in the right box of FIG. 6. At first, the difference of two LED signals and their first and second derivatives are calculated, as shown in FIG. 5. Then, the first derivative is checked for having a minimum positive gradient which exceeds a pre-defined value. At this point, a zero crossing of the second derivative are verified. Following in the time course of the signals, the minimum gradient and zero crossing should be observed with opposite sign. If one of said checks fails or does not occur within a defined movement distance of the test tape, then no edge is detected and the routine starts again with the first step.

Due to this routine, interfering objects like a finger or clothing of a user in front of the optical detector are tolerated in certain ranges. Out of the tolerance ranges, error messages may be produced.

A rising edge in the obtained optical signals occurs during tape movement from a transparent tape section 56 to a functional element 20. The detection of the rising edge follows the same scheme as the falling edge, however with opposite sign.

From the tape velocity, the sampling rate and the position of the falling and rising edges, respectively, the distance between the edges is calculated.

In a following evaluation step, the calculated distance is compared to a pre-defined distance value including a tolerance. In case the distance is within the tolerance for the standby position of the white field 48 or the active position of the test field 46, the center of the fields 46, 48 is determined from the known with of these fields and the actual tape position. If these center positions are reached, the tape drive is stopped.

In case that the calculated distance can be assigned neither to the test field nor the white field, the calculated distance is regarded as invalid. In this case, the signal processor 34 starts again to detect a falling edge.

The invention claimed is:

1. An analyte measuring system comprising:
 a test tape having a plurality of functional elements arranged thereon, the functional elements comprising at least a test field onto which a body fluid can be applied by a user; and
 a meter comprising
  a tape drive operable to advance the test tape, such that the functional elements can be successively positioned in a measuring position,
  a light source adapted to illuminate at least one measuring spot at the measuring position, and
  a measuring engine configured to receive optical signals from the at least one measuring spot for detection of the analyte in the body fluid, the measuring engine comprising a signal processor operable to determine if a test field is in the measuring position, said determining comprising determining the distance between at least two functional elements on the basis of optical signals received while advancing the test tape, and comparing the determined distance with a pre-determined distance identifying that the test field is in the measuring position.

2. The system of claim 1, wherein the light source is configured to illuminate at least two essentially non-overlapping measuring spots which are arranged one after another in the direction of tape transport.

3. The system of claim 1, wherein all of the measuring spots are arranged on one functional element when said functional element is provided in the measuring position.

4. The system according to claim 1, wherein the light source comprises one or more LEDs to illuminate a distinct measuring spot.

5. The system of claim 4, wherein at least two LEDs are provided which emit at different wavelengths.

6. The system according to claim 1, wherein the measuring engine has a sampling frequency in the range of milliseconds to record the optical signals.

7. The system according to claim 2, wherein the signal processor is operable to evaluate differences between the optical signals obtained from each of the at least two measuring spots.

8. The system of claim 7, wherein the signal processor is operable to evaluate one or more derivatives of said differences between the optical signals.

9. The system according to claim 1, wherein the signal processor is operable to derive a distance between at least two functional elements from a speed of the tape transport and a time period between consecutive edges of signal peaks in the optical signals.

10. The system according to claim 1, wherein the signal processor comprises a comparator to compare the distance between the two functional elements to the pre-determined distance.

11. The system according to claim 1, wherein the signal processor is adapted to stop the tape drive when having determined that a test field is in the measuring position.

12. The system according to claim 1, wherein the signal processor is operable to determine a difference in the level of the optical signals received from two measuring spots which are illuminated at different wavelengths.

13. The system according to claim 1, wherein the functional elements comprise reflective fields, each of which is arranged between successive test fields, and wherein the test tape is positioned in a standby state when a reflective field is in the measuring position.

14. The system according to claim 1, wherein the body fluid is blood, and wherein the analyte preferably is blood glucose.

15. An analyte measuring method comprising:
providing a test tape having a plurality of functional elements arranged thereon, the functional elements comprising at least a test field onto which a body fluid can be applied by a user;
advancing the test tape in a meter such that the functional elements are successively transported to a measuring position;
illuminating at least one measuring spot on a functional element at the measuring position;
receiving optical signals from the at least one measuring spot for detection of the analyte in the body fluid; and
determining, from optical signals obtained while advancing the test tape, if a test field is in the measuring position, wherein said determining comprises determining the distance between at least two functional elements on the basis of received optical signals, and comparing the determined distance with a pre-determined distance identifying that the test field is in the measuring position.

16. The system according to claim 1, wherein the meter is a handheld meter.

17. The system according to claim 5 wherein at least one LED emits at a wavelength in the visible region and at least one LED emits at a wavelength in the infrared region.

18. The system according to claim 10 wherein a tolerance is taken into account.

19. The system of claim 1 wherein the determining if a test field is in the measuring position comprises
obtaining an optical signal from a preceding functional element and an optical signal from a next functional element,
determining the distance between the preceding function element and the next functional element, and
determining that the next functional element is in the measuring position based on the determined distance.

20. The system of claim 1 wherein the optical signals from the functional elements indicate the leading edge and the trailing edge of a functional element; the optical signal obtained from the preceding functional element indicating the trailing edge of the preceding functional element and the optical signal obtained from the next functional element indicating the leading edge of the next functional element, the determining comprising determining the distance between the trailing edge of the preceding element and the leading edge of the next functional element.

21. The system according to claim 20, wherein the signal processor is operable to derive the distance between the preceding and the next functional elements from a speed of the tape transport and a time period between the trailing and leading edges of the optical signals.

22. The method of claim 15 wherein the determining if a test field is in the measuring position comprises
obtaining an optical signal from a preceding functional element and an optical signal from a next functional element,
determining the distance between the preceding function element and the next functional element, and
determining that the next functional element is in the measuring position based on the determined distance.

* * * * *